(12) United States Patent
Drummond

(10) Patent No.: US 6,725,966 B2
(45) Date of Patent: Apr. 27, 2004

(54) STETHOSCOPE

(75) Inventor: Thomas E. Drummond, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/134,807

(22) Filed: Apr. 29, 2002

(65) Prior Publication Data

US 2003/0201138 A1 Oct. 30, 2003

(51) Int. Cl.⁷ .............................. A61B 7/02; A61B 7/04
(52) U.S. Cl. ........................................ 181/131; 381/67
(58) Field of Search .................... 181/131, 132, 181/133, 129; 381/67; D24/133, 134

(56) References Cited

U.S. PATENT DOCUMENTS

| | | | |
|---|---|---|---|
| 3,587,776 A | | 6/1971 | Haiken |
| 3,894,169 A | * | 7/1975 | Miller ........................ 181/207 |
| 4,440,258 A | | 4/1984 | Packard |
| 4,458,778 A | * | 7/1984 | Bloom ........................ 181/131 |
| 4,475,619 A | | 10/1984 | Packard |
| 4,528,690 A | * | 7/1985 | Sedgwick .................... 381/67 |
| 4,995,473 A | * | 2/1991 | Packard ....................... 181/131 |
| 5,921,941 A | * | 7/1999 | Longobardo et al. ......... 381/67 |
| 6,308,798 B1 | * | 10/2001 | Rashman et al. ............ 181/131 |
| 6,428,886 B1 | * | 8/2002 | Lewis et al. .................. 18/131 |

FOREIGN PATENT DOCUMENTS

| | | |
|---|---|---|
| GB | 1 271 460 A | 4/1972 |
| GB | 2 268 405 A | 1/1994 |

OTHER PUBLICATIONS

U.S. patent application Ser. No. 09/948,971, filed Sep. 7, 2001, Customizable Split Stem Stethoscope and a Method for Providing Same.

* cited by examiner

Primary Examiner—Robert Nappi
Assistant Examiner—Eduardo Colon-Santana
(74) Attorney, Agent, or Firm—John A. Burtis; Daniel R. Pastirik

(57) ABSTRACT

A chestpiece for a stethoscope, the chestpiece having a novel mix of desirable properties through being fabricated from the group of materials known as "high gravity compounds." These compounds are prepared by loading various plastic resins with high density metal powders. In spite of the metallic content, appropriate compounds can be injection molded, providing economic and aesthetic advantages.

3 Claims, 1 Drawing Sheet

STETHOSCOPE

TECHNICAL FIELD

The invention relates generally to stethoscopes, and more particularly to stethoscopes having chestpieces fabricated from polymeric material.

BACKGROUND

One of the most recognizable tools in the physician's art is the stethoscope. It is a useful device in that many bodily organs emit sounds that are diagnostic, including the heart, the lungs, the arteries, and the joints. In order to be able to focus on the particular sounds emitted by the organ of interest, and to help the physician discriminate between normal and pathological sounds, stethoscope makers have tried to make more versatile instruments. In particular, much interest in the art has been paid to devices which can either emphasize or de-emphasize particular frequency ranges depending on the physician's need of the moment.

One of the best known techniques for accomplishing this desirable versatility is to incorporate more than one sound collecting microphone into the chestpiece of the stethoscope. The two most conventional types of microphones are the so-called diaphragm type, which has a thin, usually round, disc of material defining a sound collecting surface, and the so-called bell type, which as an open, concave shape, the lip of which defines a sound collecting surface, to funnel acoustic energy towards the passageways that carry sound to the ears. The bell type microphone is well adapted to convey the lowest tones, such as the main "lub-dup" of the heartbeat. Diaphragm type microphones are most typically tuned to de-emphasize those sounds, and to pass tones of slightly higher frequency. This allows the user of the stethoscope to more readily perceive the sounds typical of heart valve pathologies. One microphone of each type may be placed on the chestpiece to increase the versatility of the stethoscope.

Different materials have been used to fabricate the chestpiece. Some users prefer chestpieces manufactured from metal, which have the advantage of strength, durability, and a pleasant solidity in the hand, and both machining and casting techniques have been used for this purpose. Other users prefer chestpieces manufactured from polymeric materials, which have the advantage of lower manufacturing cost, a lower weight when hung around the user's neck, and a pleasant warmth in contact with a patient's body. Both thermoplastic and thermoset polymers have been used for this purpose. Hybrid chestpieces with portions being manufactured from one type of material and portions manufactured from the other type are common.

SUMMARY OF THE INVENTION

In one aspect, the present invention provides a chestpiece for a stethoscope, the chestpiece having a novel mix of desirable properties through being fabricated from the group of materials known as "high gravity compounds" or "HGCs." These compounds are prepared by loading various plastic resins with high density metal powders. In spite of the metallic content, appropriate HGCs can be injection molded, allowing chestpieces according to the present invention to reap the advantage of lower fabrication costs that injection molding provides.

Another advantage that flows from this property is the ability to select aesthetically pleasing shapes beyond those that can be achieved at a practical cost with machining. The use of HGCs also expands the range of colors available compared with metals of similar density, also adding to the aesthetic nature of the stethoscope.

More specifically, the invention provides a chestpiece for stethoscope having a body having at least one sound collecting microphone mounted thereon, the body comprising a high gravity compound, generally having a density of at least about 3 grams/cc. A density of at least about 4.5 grams/cc is also considered useful. In many preferred embodiments, the sound collecting microphone is a microphone of the bell type. As will be discussed with more particularity below, is believed that the higher density is particularly valuable in enhancing the sound gathering qualities of a bell type microphone. Other preferred embodiments will also have a microphone of the diaphragm type, and a mechanism of selecting which microphone is active.

BRIEF DESCRIPTION OF THE DRAWINGS

In the several figures of the attached drawing, like parts bear like reference numerals, and.

DETAILED DESCRIPTION OF ILLUSTRATIVE EMBODIMENTS OF THE INVENTION

Figure 1:
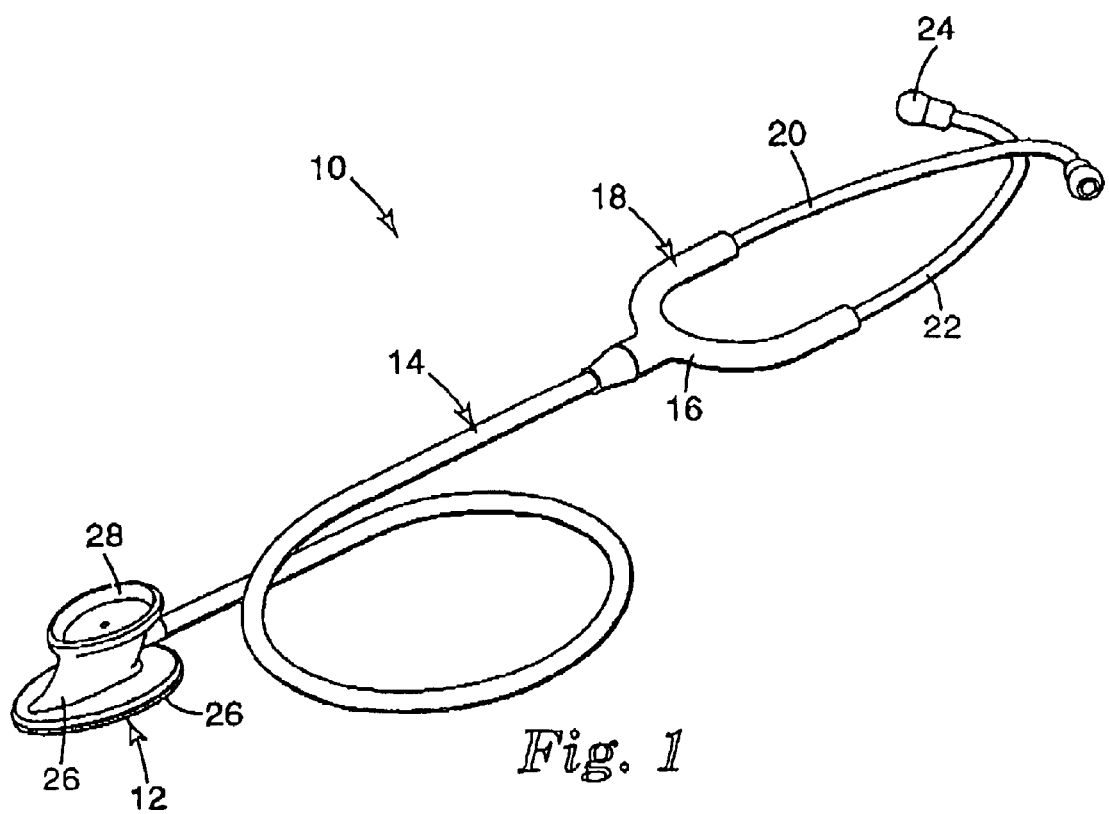
FIG. 1 is a perspective view of a stethoscope according to the present invention.

Referring to FIG. 1, a perspective view of a stethoscope 10 is shown. The stethoscope has a chestpiece 12 connected to a binaural 14 which divides at yoke 16 into a headset 18 having dual sound transmitting tubes 20 and 22 terminating in ear tips 24. The chestpiece 12 includes a central body 26 supporting both a bell-type microphone 28 and a diaphragm-type microphone 30.

Figure 2:
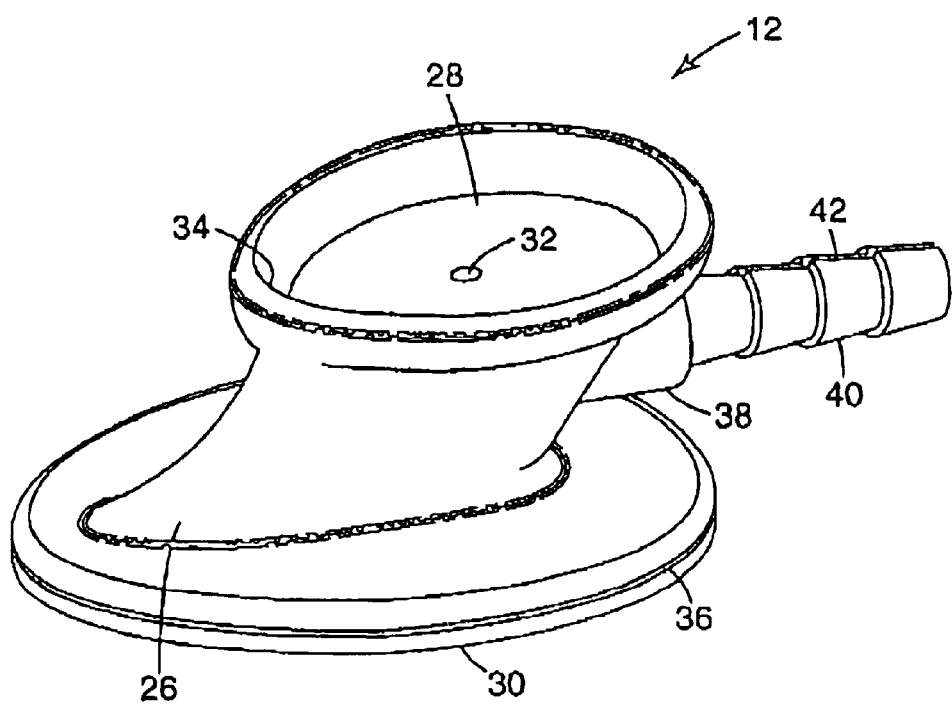
FIG. 2 is a perspective view of the chestpiece of the stethoscope of FIG. 1, shown in isolation.

Referring now to FIG. 2, a perspective view of the chestpiece 12 of the stethoscope 10 of FIG. 1 is illustrated in isolation. In this view, it is more readily appreciated that bell-type microphone 28 includes a sound transmitting passageway 32, and a flange 34 for receiving an optional non-chill ring (not shown). The diaphragm-type microphone 30 conveniently includes a recess 36 for securing a retaining ring (not shown) for retaining a diaphragm. This is preferably either a lightly fixed diaphragm generally as described in U.S. Pat. No. 4,475,619, "Stethoscope with floating diaphragm," or a movable diaphragm, sometimes called a "tunable" diaphragm, generally as described in U.S. Pat. No. 4,440,258, "Tunable stethoscope." Sound energy gathered from the body by either of the two microphones is directed through a sound transmitting passageway, e.g. 32, and is conducted through a stem 38 to the binaural 14 (as illustrated in FIG. 1). Conveniently, the microphone to be used for collecting sound energy is selected by rotating the stem 38 within the body 26. The stem 38 is conveniently indexed into one of its two positions by means of a detent mechanism, with many suitable designs being known to the skilled artisan. The illustrated stem 38 has several barbs 40 and a longitudinal groove 42, to permit the stem 38 to more firmly hold the binaural 14 during rotation of the stem to effect such indexing. If the use of a dual lumen binaural is contemplated, the stem 38 can also be of the split style described in copending and coassigned U.S. patent application Ser. No. 09/948,971, "Customizable split stem stethoscope and a method for providing same."

The body 26 of the chestpiece 12 according to the present invention, and whatever sound gathering microphones, e.g.

28 and 30, are attached to the body 26, are fabricated from moldable materials generally known as High Gravity Compounds (HGCs). These compounds are prepared by loading a base plastic resin or resin mixture with at least one high density metal powders such as tungsten. HGC's are presently available in a number of base resins, including polypropylene, nylon, acrylonitrile butadiene styrene (ABS), polyurethanes, polyphenylene sulfide, polyeretherketone (PEEK) to name a few. Currently considered preferred is a HGC comprising semi-crystalline thermoplastic polyester resins based on polybutylene terephthalate (PBT) polymers, loaded with tungsten powder to a specific gravity of 5 grams/cc, commercially available as Valox™ NBV 401 from GE Plastics of Pittsfield, Mass. HGCs are available with densities ranging from low levels associated with unloaded plastic resins up to as high as 11 grams/cc, which is a higher specific gravity than the stainless steel typically utilized for machined stethoscope chest pieces. It may also be convenient to fabricate the stem from HGCs as well, and it has been found that the use of Valox™ 325, also available from GE Plastics, is convenient for that purpose.

It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

I claim:

1. A chestpiece for a stethoscope, comprising:

a body having at least one sound collecting microphone mounted thereon, the body comprising a high gravity compound comprised of a resin and a metal powder, wherein the resin comprises semi-crystalline thermoplastic polyester resins based on polybutylene terephthalate polymers, and the metal comprises tungsten powder, the high gravity compound having a specific gravity of 5 grams/cc.

2. The chestpiece according to claim 1 wherein the sound collecting microphone is a microphone of the bell type.

3. The chestpiece according to claim 2 further comprising a microphone of the diaphragm type.

* * * * *